United States Patent [19]
Cooper et al.

[11] Patent Number: 5,856,869
[45] Date of Patent: Jan. 5, 1999

[54] DISTRIBUTED BRAGG REFLECTOR DIODE LASER FOR RAMAN EXCITATION AND METHOD FOR USE

[75] Inventors: John B Cooper, Virginia Beach; Philip E. Flecher, Dale City, both of Va.; William T. Welch, Ashland, Ky.

[73] Assignee: Ashland Inc, Ashland, Ky.

[21] Appl. No.: 657,481

[22] Filed: May 29, 1996

Related U.S. Application Data

[63] Continuation-in-part of Ser. No. 432,559, May 1, 1995.
[51] Int. Cl.$^6$ .............................. G01J 3/44; G01N 21/65
[52] U.S. Cl. ............................................................ 356/301
[58] Field of Search ............................................. 356/301

[56] References Cited

U.S. PATENT DOCUMENTS

| | | | |
|---|---|---|---|
| 5,455,673 | 10/1995 | Alsmeyer et al. | 356/301 |
| 5,537,432 | 7/1996 | Mehuys et al. | 372/50 |

OTHER PUBLICATIONS

"Applications of Raman Spect. to Ind. Processes"; S. Farquharson et al.; SPIE vol. 1681;Optically Based Methods for Process Analysis; 1992; 276–290.

"Remote Raman Analysis for Process Monit. Applications"; F. Purcell et al.; SPIE vol. 1681; Optically Based Methods for Process Analysis; 1992; 149–158.

"Instrumental Tech. for Infrared and Raman Vibrational Optical Act."; L.A.Nafie; SPIE vol. 1681; Optically Based Methods for Process Analysis; 1992; 29–40.

Simultaneous Multi–point Fiber–optic Raman Sampling for Chem. Proc. Control Using Diode Lasers and a CCD Detector; S. M. Angel et al.; SPIE vol. 1587; Chem. Biochem. and Envir. Fiber Sensors III; 1991; 219–231.

"In Situ Fiber–optic Raman Spect. of Org. Chem. in a Supercritical Water Reactor"; M. L. Myrick et al.; Journal of Raman Spectr. vol. 25; 1994; 59–64.

"Advances in Surface–Enhanced Raman Spect. for Hazard. Waste Monitoring"; E. A. Wachter et al.; SPIE vol. 1336; Raman an Luminescence Spectro. in Tech II; 1990; 156–262.

"A New Device for Raman Difference Spectr. and Its Appl. to Observe Freq. Shifts Due to Isotope Mixing"; K. Kamogawa et al.; J. Phys. Chem.; 1990, 94 3916–3921.

"In Situ Cure Monit. of Epoxy Resins Using Fiber–Optic Raman Spect."; R. E. Lyon et al.; Applied Polymer Science; vol. 53; 1994; 1805–1812.

"Remote, High Sensit. Raman Spectr. with Fiber Optics, Diode Lasers, and CCD Spectrometers"; R. L. McCreery; SPIE vol. 1637; Environmental and Process Monit. Tech.; 1992; 208–215.

Fiber–optic Sensors Using Raman & Surface–enhanced Raman Spectro.; S. M. Angel et al.; American Chemical Society; 2181–2/92/0072; 1992, 72–89.

"Uranium Det. by Remote Tiem–Resolved Laser–induced Fluorescence"; C. Moulin et al.; Applied Spectroscopy; vol. 47; No. 12, 1993; 2007–2011.

(List continued on next page.)

*Primary Examiner*—F. L. Evans
*Attorney, Agent, or Firm*—Richard C. Willson, Jr.; Richard D. Stone; A. J. Adamcik

[57] ABSTRACT

A distributed Bragg reflector (DBR) diode laser is used as excitation source for fiber optic Raman spectroscopy utilizing charge coupled device (CCD) detection and an image-corrected spectrograph. The DBR diode laser is superior to index guided diode lasers (Fabry-Perot) for elimination of mode hopping, elimination of frequency hysteresis as a function of both temperature and current changes, and reduction in laser broadband emission. These advantages allow the DBR laser to be used in industrial process control applications which are too demanding for index guided diode lasers.

15 Claims, 7 Drawing Sheets

OTHER PUBLICATIONS

Fiber–optic Sampling Combined with an Imaging Spectrograph for Routine Raman Spect.; C. D. Newman et al.; Applied Spectro.; vol. 46; No. 2; 1992; pp. 262–264.

Near–infrared Fourier Transform Raman Spectro. Using Fiber–optic Assemblies; E. N. Lewis et al.; Anal. Chem.; 1988; 60; 2658–2661.

"Use of a Mono–fiber Optrode in Remote and in Situ Measurements by the Raman Laser/Fiber Optics (RLFO) Method"; N. Huy et al.; Appl. Spec.; vol. 47; No. 12; 1993; 2013–2016.

Det. of Organics on Metal Surf. by Raman Spectr.; C. Tseng et al.; Appl. Spect. vol. 47; No. 11; 1993; 1767–1771.

"Remote–Raman Spectro. at Intermediate Ranges Using Low–Power CW Lasers"; S. M. Angel et al.; Appl. Spect.; vol. 46; No. 7, 1992; 1085–1091.

"Near Infrared Raman Spect. with a 783 nm Diode Laser and CCD Array Detect."; J. M. Williamson; Appl. Spect.; vol. 43; No. 3; 1989; 372–375.

"Near–infrared Raman Spect. of Liq. & Solids with a Fiber–optic Sampler, Diode Laser, and CCD Detector"; C. D. Allred et al.; Appl. Spect.; vol. 44; No. 2; 1992; 262–264.

"Determination of Octane Numbers & RVP of Commercial Petroleum Fuels Using FT–Raman Spectroscopy and Partial Least–Squares Regression Analysis" by John B. Cooper et al.; Anal. Chem., vol. 67, #22; Nov. 15, 1995; pp. 4096–4100.

"Elimination of Mode Hopping & Frequency Hysteresis in Diode Laser Raman Spectroscopy: The Advantages of a DBR Diode Laser for Raman Excitation" by John B. Cooper et al.; Appl. Spect., vol. 49, No. 11, 1995; pp. 1692–1698.

Remote Fiber–Optic Raman Analysis of Xylene Isomers in Mock Petroleum Fuels Using a Low–Cost Dispersive Instrument & Partial Least–Squares Regression Anal. by John B. Cooper et al.; Appl. Spect., vol. 49, No. 5, 1995; pp. 586–592.

ation Ser. No. 08/432,559, filed May 1, 1995.
DISTRIBUTED BRAGG REFLECTOR DIODE LASER FOR RAMAN EXCITATION AND METHOD FOR USE

CROSS REFERENCE TO RELATED APPLICATIONS

This application is a continuation-in-part of U.S. application Ser. No. 08/432,559, filed May 1, 1995.

Cross references to related application, U.S. patent application Ser. No. 08/432,559, filed May 1, 1995 (docket number 6500AUS); and U.S. patent application Ser. No. 08/449,326, filed May 24, 1995 (docket number 6516AUS, now U.S. Pat. No. 5,596,196); U.S. patent provisional application 60/004512, filed Sep. 29, 1995 (docket number 6518AUS); and U.S. 60/002649, filed Aug. 22, 1995 (docket number 6523AUS) relate to the general field of the present invention.

BACKGROUND OF THE INVENTION

I. FIELD OF THE INVENTION

This invention relates to the field of Raman spectroscopy and to lasers for Raman excitation.

II. DESCRIPTION OF THE PRIOR ART

Sample fluorescence hinders Raman spectroscopy applications (especially those which use visible laser excitation) by masking the Raman signal and making vibrational characterization difficult if not impossible. A common way to avoid this problem is with the use of NIR laser excitation (C. J. Frank, D. C. Redd, T. S. Gansler, and R. L. McCreery, *Anal. Chem.*, 66, 319 (1994)). NIR laser excitation has the additional advantage of high transmittance through optical fibers which can be used for remote spectroscopy. Traditionally, the sources for such excitation in the laboratory have been either dye lasers or solid state lasers, both of which are large, expensive, have limited lifetimes, and have high operating costs.

More recently, laboratories have begun to report the use of diode lasers as the excitation source (R. L. McCreery, Proc. *SPIE-Int. Soc. Opt. Eng.*, 1637 (Envir. Process Monit. Technol.), 208 (1992); C. D. Allred and R. L. McCreery, *Appl. Spectrosc.*, 44, 1229 (1990); C. H. Tseng, C. K. Mann, and T. J. Vickers, *Appl. Spectrosc.*, 47, 1767 (1993); S. M. Angel, T. J. Kulp, and T. M. Vess, *Appl. Spectrosc.*, 46, 1085 (1992); J. B. Cooper, J. Aust, C. Stellman, K. Chike, and M. L. Myrick, *Appl. Spectrosc.*, 50, 567 (1994); J. M. Williamson, R. J. Bowling, and R. L. McCreery, *Appl. Spectrosc.*, 43, 372 (1989); C. J. Frank, D. C. Redd, T. S. Gansler, and R. L. McCreery, *Anal. Chem.*, 66, 319 (1994); S. M. Angel, M. L. Myrick, and T. M. Vess, *Proc. SPIE-Int. Soc. Opt. Eng.*, 1435 (Opt. Methods Ultrasensitive Detect. Anal.: Tech. Appl.), 72 (1991); N. Yamamoto, W. Z. Huang, and H. Horinaka, Jpn. *J. Appl. Phys.*, Part 1, 32 (Suppl. 32-3, Proceedings of the 9th International Conference on Ternary and Multinary Compounds, 1993), 123 (1993); H. Horinaka and N. Yamamoto, Jasco Rep., 34, 1 (1992); H. Horinaka, N. Yamamoto, and H. Hamaguchi, *Appl. Spectrosc.*, 46, 379 (1992); Y. Wang and R. L. McCreery, *Anal. Chem.*, 61, 2647 (1989); S. M. Angel and M. L. Myrick, *Anal. Chem.*, 61, 1648 (1989); A. Rubens, B. De Castro, and P. R. B. Pedreira, *Opt. Commun.*, 62, 348 (1987)). These lasers offer single mode NIR output (780–860 nm) at relatively high optical power (150 mW), they are compact (the laser itself is ~1.3 cm in diameter and 2 cm thick, the heat sink is ~10×5×5 cm, and the power supply and temperature controller unit is ~30×30×13 cm), and they are inexpensive ($1000–$2000 for laser and heat sink and $1000–$5000 for controller). In addition, lifetimes are typically two to three orders of magnitude greater than conventional lasers. Diode laser Raman investigations reported in the literature have been confined to the use of Fabry-Perot type (index guided) lasers. In this type of laser, an active region of GaAlAs is "sandwiched" between a p-doped layer of GaAlAs and an n-doped layer of GaAlAs. When a voltage is applied across this sandwich structure, current is injected and subsequent electron/hole pair re-combination in the active region give rise to photon emission. Above the current threshold (typically 30 mA) population inversion is achieved giving the resultant laser action. The higher index of refraction of the active region relative to the doped regions act to constrain the emitted photons to the active region thus forming the cavity for the laser, hence the common name "index guided" laser.

III. PROBLEMS PRESENTED BY PRIOR ART

For an index guided diode laser, the frequency of the emitted photons is totally dependent on the band gap of the semiconductor device, and it is this dependence which gives rise to many of the problems associated with diode laser sources for spectroscopy. Since the band gap is dependent on the temperature of the device, changes in temperature result in changes in laser wavelength. For spectroscopic applications, a thermoelectric cooler is thus required for the laser. Typically, the laser wavelength shifts 0.3 nm with every 1° C. change in temperature. Unfortunately, the change in band gap with temperature is often plagued with hysteresis so that when a laser is shut down or the temperature is changed from initial conditions, reproducing the initial conditions does not necessarily reproduce the initial wavelength. Under such conditions, Raman spectra acquired at a set spectrograph grating position will have an apparent shift when compared to previously acquired spectra at the same temperature.

The band gap is also dependent on the injection current. As the current level is changed in order to increase or decrease the optical power output, regions of instability are often encountered where the laser wavelength will shift, or will emit multiple wavelengths or even oscillate between two wavelengths at an undetermined rate. These events are often referred to as "mode hops". Even when a region of stability (with regards to the current and the optical output frequency) is attained, there is no guarantee that the device will remain stable under these conditions at a later date after some change in conditions has occurred. Finally, the optical output also can be destabilized by photons which are back reflected into the laser by collimating optics, pigtails, etc. (also referred to as optical feedback). The net result is a laser which gives highly ir-reproducible behavior over the course of time, thus limiting its use in any type of industrial control application.

A recent improvement in diode lasers has come with the development of external cavity diode lasers. In this type of laser, an external grating is used to provide selective feedback to the active region so that lasing only occurs at one wavelength, the remaining emission wavelengths are dispersed outside of the cavity by the grating. By changing the position of the grating, the laser wavelength can be tuned to a desired value. Typically the tuning range is 20 nm with a laser line width of 1–5 MHz. The selective feedback also eliminates hysteresis and mode hopping. Unfortunately, these lasers remain expensive, typically costing >$20,000. Additionally, the external grating requires the laser to be larger and less robust than conventional diode lasers.

SUMMARY OF THE INVENTION

I. GENERAL STATEMENT OF THE INVENTION

According to the invention, a distributed Bragg reflector (DBR) diode laser is used as excitation source for fiber optic Raman spectroscopy utilizing charge coupled device (CCD) detection and an image-corrected spectrograph. The DBR diode laser is superior to index guided diode lasers (Fabry-Perot type) for elimination of mode hopping, elimination of frequency hysteresis as a function of both temperature and current changes, and reduction in laser broadband emission. These advantages allow the DBR laser to be used in industrial process control applications which are too demanding for index guided diode lasers.

This invention most preferably comprises the use of a newly developed distributed Bragg reflector (DBR) diode laser which provides selective feedback via an internal grating. The "sandwich structure" of the DBR laser is similar to the index guided diode laser, but instead of relying on the index guiding behavior of the facets adjoining the active region, the DBR laser has an internal grating etched into the cavity. This internal grating provides selective feedback to the active region over a very narrow spectral range which increases the spectral and temperature stability of the laser. The laser line width is less than 4 MHz. The DBR laser comes in conventional diode laser package (e.g., TO3 can) and can be driven using conventional diode laser drivers. The laser is commercially available for approximately $3,000 and eliminates the problems discussed above which are associated with the use of index guided diode lasers for Raman excitation.

The distributed Bragg reflector type of diode laser utilizes an internal Bragg reflector grating in the active region to select and stabilize the operating laser wavelength. The output laser wavelength shifts as a function of temperature according to the following equation:

$$\lambda_p = \lambda_{po} + (\Delta\lambda/\Delta T)(T - T_O) \quad \text{eq. (1)}$$

where $\lambda_p$ is the peak wavelength reflected by the Bragg grating at temperature T, $\lambda_{po}$ is the peak wavelength reflected by the Bragg grating at temperature $T_O$, and $\Delta\lambda/\Delta T$ is 0.07 nm/° C. Although the laser output wavelength is a function of temperature, the wavelength shift is small in comparison to an index guided diode laser. Significantly, there is no hysteresis in the temperature tuning of the DBR output wavelength. Therefore, using a temperature controller, a high level of laser wavelength reproducibility can be obtained. This is in stark contrast to the index guided diode laser which exhibits significant hysteresis upon temperature changes. In practical terms this means that the DBR laser can be shut down and restarted without shifting the output wavelength.

The output wavelength of the DBR laser is also a function of the drive current according to the following relationship:

$$\lambda = \lambda_O + (\Delta\lambda/\Delta I)(I - I_O) \quad \text{eq. (2)}$$

where $\lambda$ is the wavelength at current I, $\lambda_O$ is the wavelength at current $I_O$, and $\Delta\lambda/\Delta I$ ranges from 0.003 to 0.1 nm/mA. The exact value $\Delta\lambda/\Delta I$ depends upon the specific laser diode and its bias level. For a particular device and driver, the value of $\Delta\lambda/\Delta I$ will be fixed. The linear dependence of the wavelength on drive current is valid when the changes in drive current are relatively small (1–5 mA). Under these conditions, the 852 nm output will not vary by more than 0.7 cm$^{-1}$. When the power supply is used in light mode, the current does not typically vary by more than 1 mA. Such variation would result in a maximum laser shift of 0.14 cm$^{-1}$ which will not affect the resultant Raman spectrum at 10 cm$^{-1}$ resolution. This is consistent with our results. When the drive current is varied dramatically (10–40 mA), applicants have observed the output to mode hop (i.e., a nonlinear dependence of the wavelength on drive current). However, no hysteresis is evident, i.e. a return to the original drive current always results in a return to the original output wavelength. This is atypical for index guided diode lasers which exhibit significant hysteresis.

Although applicants have not tried to deliberately introduce back reflections into the laser cavity (this is not recommended since it has been known to cause diode failure in the case of index guided devices), in our laboratory setup, the DBR laser will not mode hop when the temperature and current remain constant, while the index guided diode laser often will. This is probably due to an increased dependence of the index guided device on optical feedback. Such an effect would be consistent with previously reported results (D. W. Nam and R. G. Waarts, Laser Focus World, 30, 49 (1994)).

There are a few disadvantages of a DBR laser relative to an index guided diode laser. Single mode index guided diode lasers are available with high optical powers (up to 200 mW) across a range of optimum wavelengths (typically 780–860 nm). The DBR laser is presently available at one wavelength (852 nm) in this region with an optical power rating of 100 mW. The question of optical power is not as significant since both types of lasers deliver sufficient power for most Raman applications. The disadvantage of exciting at 852 nm relative to shorter wavelengths is two-fold. First, the Raman scattering intensity is proportional to the frequency of the laser raised to the fourth power. Relative to excitation near 800 nm, 852 nm excitation will result in ~80% of the Raman scattering intensity. Perhaps more importantly, detection of longer wavelengths with a silicon based detector such as a CCD results in a weaker signal due to a decrease in detector quantum efficiency. For example, using the present setup it is possible to acquire the CH stretching region of toluene when using an 805 nm index guided diode laser (albeit the signal is very weak), while for the DBR laser the CH stretching region occurs at ~1,150 nm, and the signal is not detectable since the photon energy is less than that of the silicon detector band gap. However, in the fingerprint region of the Raman spectrum, the difference in quantum efficiency for silicon based CCDs is not as significant. For Applicants' present experimental setup, the decrease in scattering intensity for the DBR laser (852 nm) relative to the index guided diode laser (805 nm) is by a factor of two. The lower quantum and scattering efficiencies are slightly offset by the dispersion efficiency of our system, since the grating is blazed at 1 $\mu$m. Although Raman excitation at longer wavelengths results in a slight decrease in signal intensity, it generally benefits from a decrease in sample fluorescence which is a primary reason for NIR excitation. This suggests that for some applications in which an index guided diode laser might be used, the present restriction of the DBR laser to output at 852 nm is not necessarily a disadvantage. Regardless, as demand increases, it is likely that in the future the DBR will be available at shorter wavelengths, thus providing an uncompromised alternative to index guided diode lasers.

II. UTILITY OF THE INVENTION

The invention is useful for spectroscopy, preferably Raman spectroscopy and most particularly for determination of physical and chemical properties and constituent concentrations, preferably of hydrocarbons and other organic mixtures, e.g., liquid fuels, most preferably for on-line and at-line control of blending and other flow processes, such as reforming, hydrotreating, extraction, distillation, and production of specific petrochemicals.

Table A summarizes preferred, more preferred and most preferred parameters of the composition of the invention.

TABLE A

COMPOSITIONS

| Parameter | Conventional | Preferred | More Preferred | Most Preferred |
|---|---|---|---|---|
| State | Any | Gases | Solids | Liquids |
| Gaseous Compositions | Any | Any | Organic | Inorganic |
| Liquid Compositions | Any | Organic | Subst. or unsubst. hydrocarbon | Hydrocarbon fuels |
| Solid Compositions | Any | Any | Organic | Inorganic |

Table B summarizes preferred, more preferred and most preferred parameters of the apparatus of the invention.

TABLE B

APPARATUS

| Parameter | Conventional | Preferred | More Preferred | Most Preferred |
|---|---|---|---|---|
| Laser | Index Guided Diode Laser | Diode Laser with grating | Diode Laser with internal grating | Distributed Bragg Reflector Dioide Laser |
| Spectrometer | Raman | Any | | Raman |
| Spectral Region of Emitted Wavelength | Visible | NIR | NIR | NIR |
| Detector | Any | Single element detector | Multi-element array detector | Silicon CCD |

DESCRIPTION OF THE PREFERRED EMBODIMENTS

EXAMPLE 1

EXPERIMENTAL

The instrumental setup for fiber optic Raman spectroscopy utilizing diode lasers has been previously described (J. B. Cooper, P. E. Flecher, T. M. Vess, and W. T. Welch, *Appl. Spectrosc.*, 49, 586 (1995)). Both the index guided and the DBR GaAlAs diode lasers are purchased from SDL Inc. An SDL 800 series power supply/temperature controller is used to drive both lasers. During all experiments (with the exception of the temperature jump experiments) both of the diode laser temperatures are maintained at −10° C. For the DBR laser, this gave an optical output of 852 nm, while that for the index guided diode laser is 805 nm. For mode hopping experiments the lasers are operated in either current mode (constant current) or light mode (constant power). For current mode experiments the drive current is nominally set at 100 mA. When the lasers are run in light mode, the output power is set so that the drive current is ~100 mA. Under this condition the output power is ~100 mW for the DBR laser and ~80 mW for the index guided diode laser. Dielectric bandpass filters are used to remove broadband emission from the lasers and are obtained from both Janos Technology and Chroma Technology. The bandpass is 2 nm (FWHM) with an optical density of 4 outside of the bandpass, and is centered at either 805 or 852 nm. Holographic notch filters at 805 nm and 852 nm are used to filter out the laser line from the collected Raman signal and are purchased from Kaiser Optical Systems, Inc. All filters are angle tuned for maximum performance. A Chromex model 250IS ¼ meter spectrograph with a 300 groove/mm grating blazed at 1 micron is used to disperse the Raman signal. An ST6-UV CCD detector (Santa Barbara Instruments Group) thermoelectrically cooled to −38° C. is used to detect the dispersed signal. This detector consists of 750 horizontal pixels (12 micron widths)×350 vertical pixels. Typically, the pixels are binned on chip by 2 in the horizontal direction and by 350 in the vertical direction giving a total of 375 super pixels. For the long term stability test of the DBR laser, no binning is performed.

Figure 7:
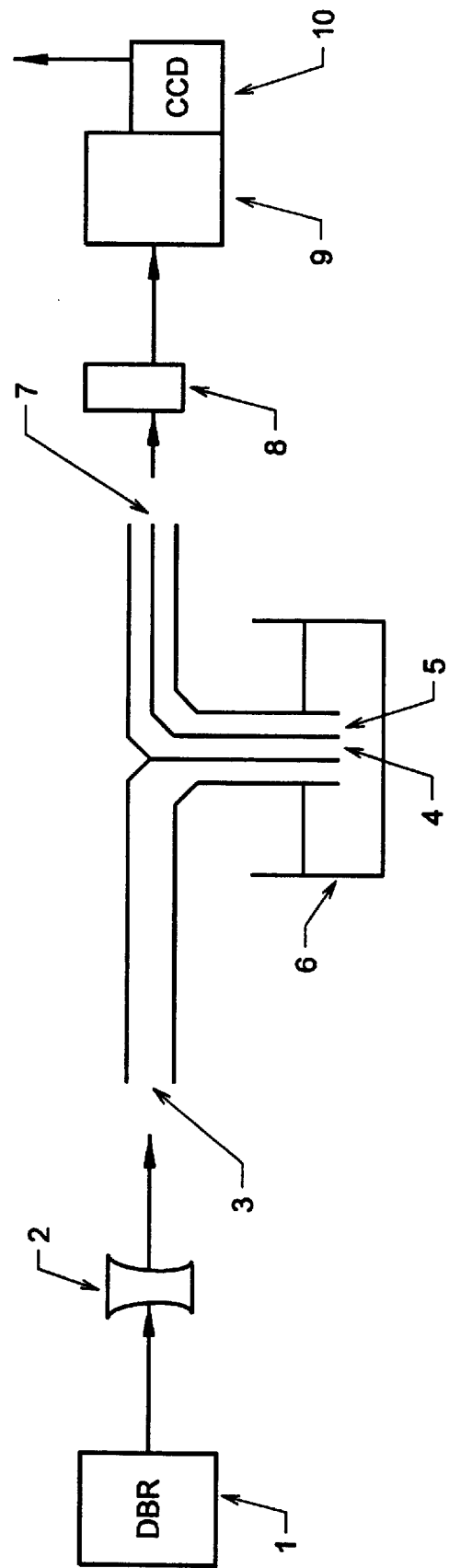
FIG. 7 is a schematic illustration of the apparatus of the invention.

Analytical grade toluene was purchased from Aldrich. Spectra are obtained by immersing the fiber optic probe directly into the sample. For all spectra, the incident power at the sample is ~40–70 mW. The spectral resolution for the described system is ~10 cm$^{-1}$ (3 cm$^{-1}$ for the long term stability test of the DBR laser). Spectral frequencies for a given grating position are calibrated by regressing the accepted Raman shifts for toluene (F. R. Dollish, W. G. Fately, and F. F. Bentley, *Characteristic Raman Frequencies of Organic Compounds* (John Wiley and Sons, N.Y., 1974) p. 363) against the detector pixel numbers. Spectral intensities are not corrected for detector or filter response. The ambient temperature during all experiments ranged from 23°–25° C. "FIG. 7 illustrates the setup of the invention schematically. Accordingly, there is shown a radiation source 1, in this case a GaAlAs DBR diode laser having an internal Bragg reflector grating. The radiation is filtered with dielectric band pass filter 2 and is sent into the proximal end of the optic fiber 3. The probe 4 consists of the distal end of the fiber 3 and proximal ends of collection fibers 5. At the end of the probe 4, the laser energy exits the optic fiber and the Raman scattered light produced from the fluid sample in sample holder 6 is collected by the proximal ends of the collection fibers 5. The Raman signal from the distal ends 7 of the collection fibers 5 is filtered with a holographic notch filter 8 before focusing on the spectrograph 9. A charge coupled detector 10 is used to detect the signal, and a signal may be output to appropriate treatment."

EXPERIMENTAL RESULTS

Using an index guided diode laser, the Raman spectrum of toluene is continuously acquired over a two hour period using a one-minute integration period for each spectrum. Examination of the resulting spectra indicates that the laser hops to a new frequency at least four times during the acquisition time (FIG. 1b). After each of these mode hops, the laser remains at the new frequency for several spectral acquisitions. Thus, out of 120 acquired spectra, no more than 33 are identical. In such a Raman experiment, it would be impossible to determine the Raman shift of an unknown sample since the laser frequency is unknown.

Applicants use this laser on a continual basis for over one year and find these results to be typical. In Applicants' experiments, the mode hops usually manifest themselves in one of three ways: 1) the laser hops to a new frequency during the acquisition period resulting in a spectrum which is the sum of two offset spectra; 2) the laser oscillates between two frequencies during the integration period resulting in a single broadened spectrum; and 3) the laser hops to a new frequency for the entire integration period resulting in a spectrum which is shifted with respect to spectra acquired prior to the mode hop. Any of these manifestations lower the reliability of the system in a process control environment.

Figure 1A:
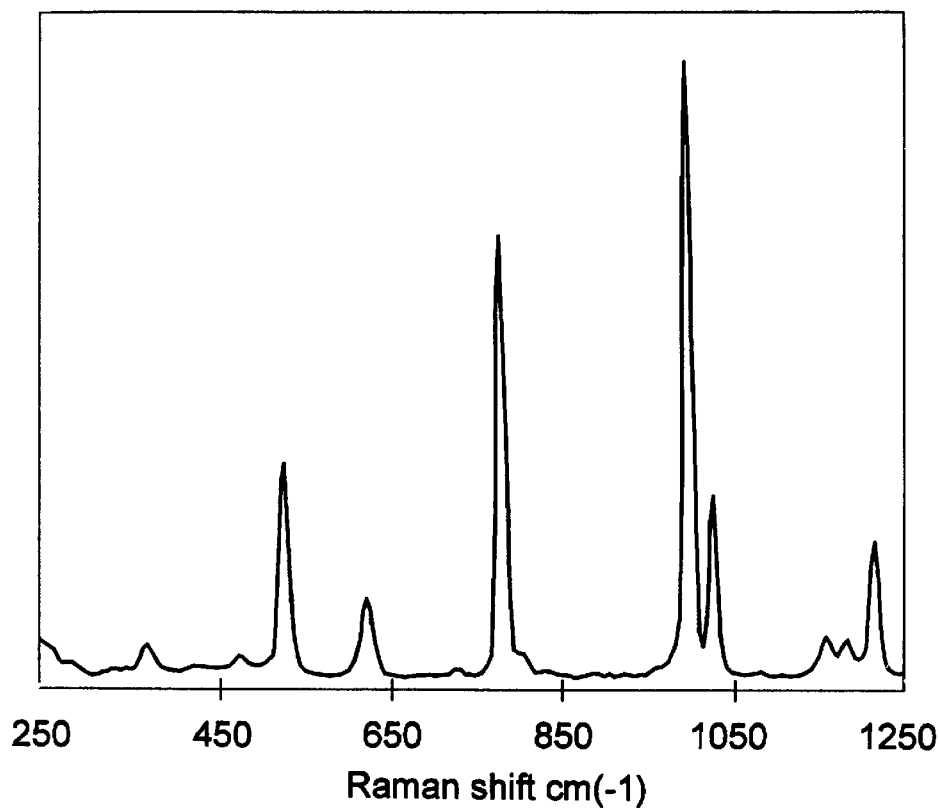
FIGS. 1a and 1b are plots of Raman spectra of toluene collected using either a DBR laser (FIG. 1a) or index guided diode laser (FIG. 1b) for excitation. Spectra are taken continuously over a two-hour period using a one-minute spectral integration period. For the DBR laser, no mode hops are observed and the Raman shift can be accurately determined as shown. For the index guided diode laser, the frequent mode hops prevent the Raman shift from being determined. Six representative spectra are shown in each plot.
Figure 1B:
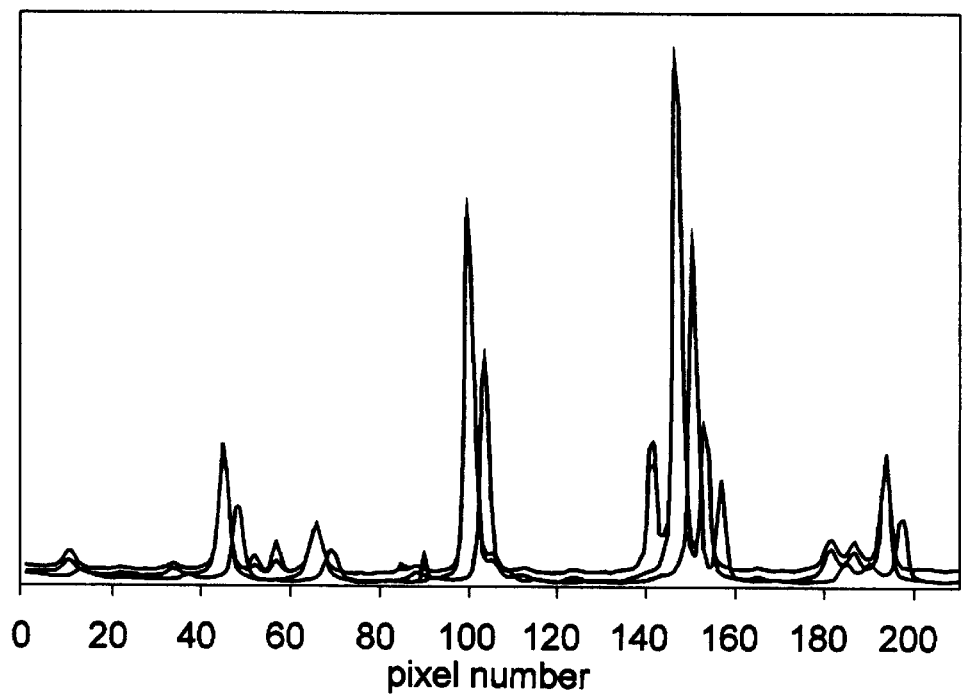
Figure 2:
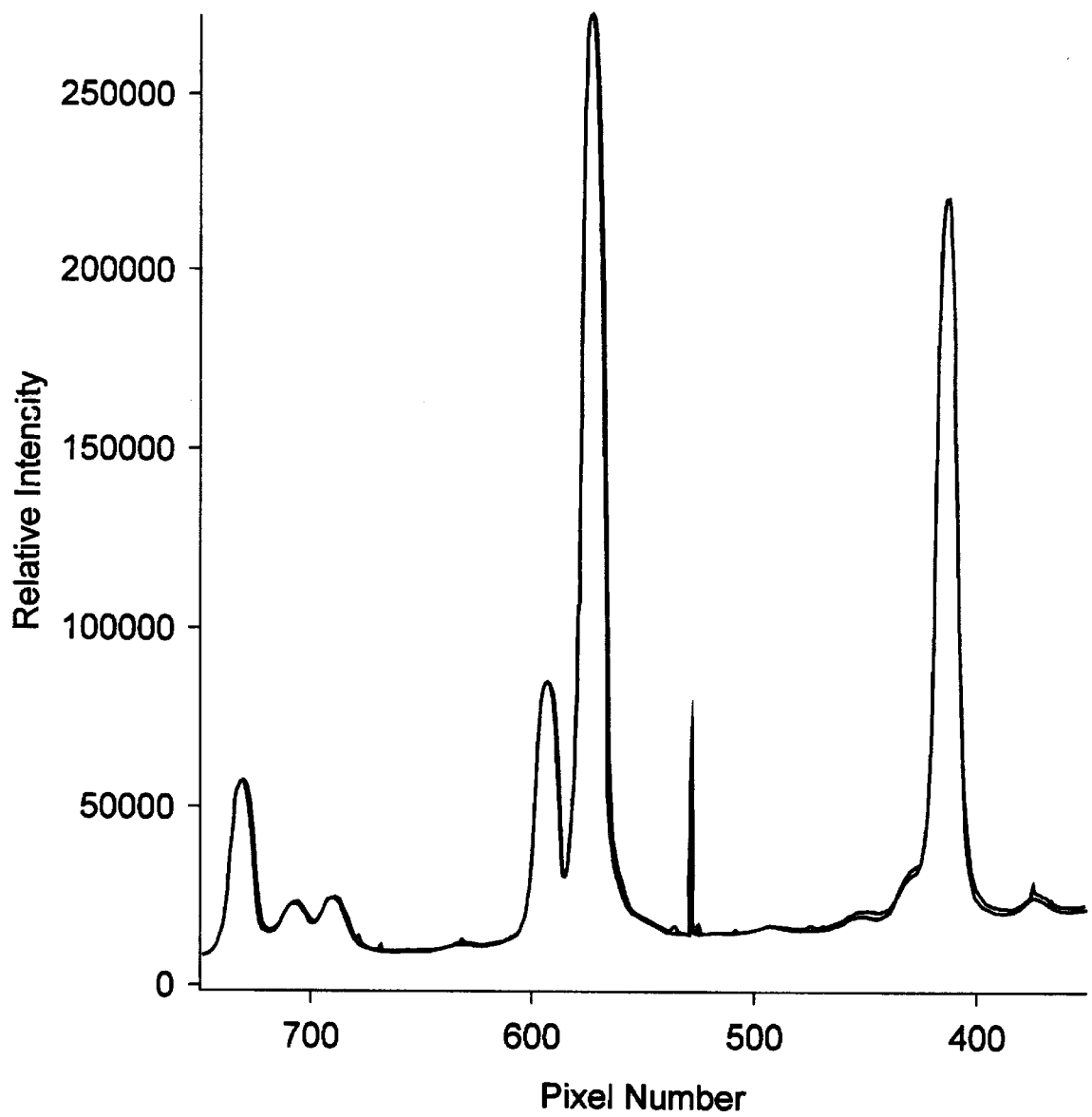
FIG. 2 is a plot of Raman spectra of toluene acquired using a DBR laser. The 360 displayed spectra are acquired continuously every ten minutes over the course of three days. The slight shift of the peaks with respect to the CCD pixel numbers is due to thermal expansion of the spectrograph. Small spikes are due to unfiltered cosmic rays. No CCD pixel binning was performed.
Figure 3:
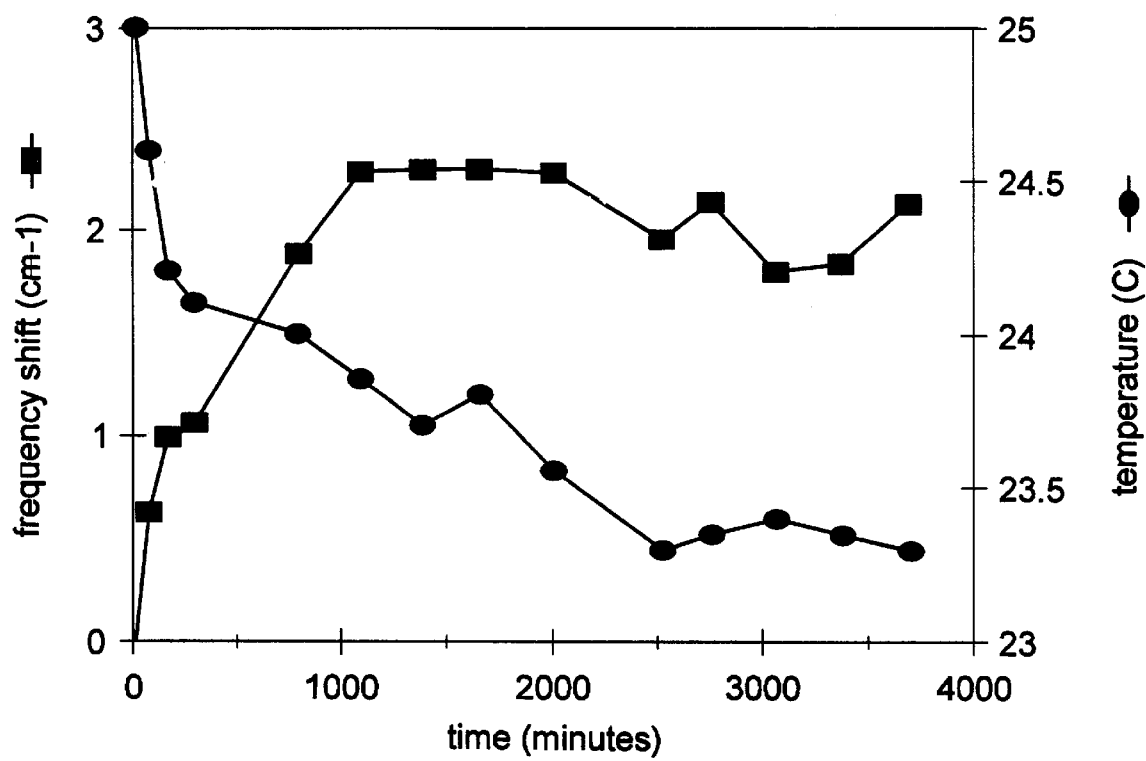
FIG. 3 is a plot of DBR excited Raman spectra (FIG. 3) frequency shifts as a function of time and room temperature.
Figure 4:
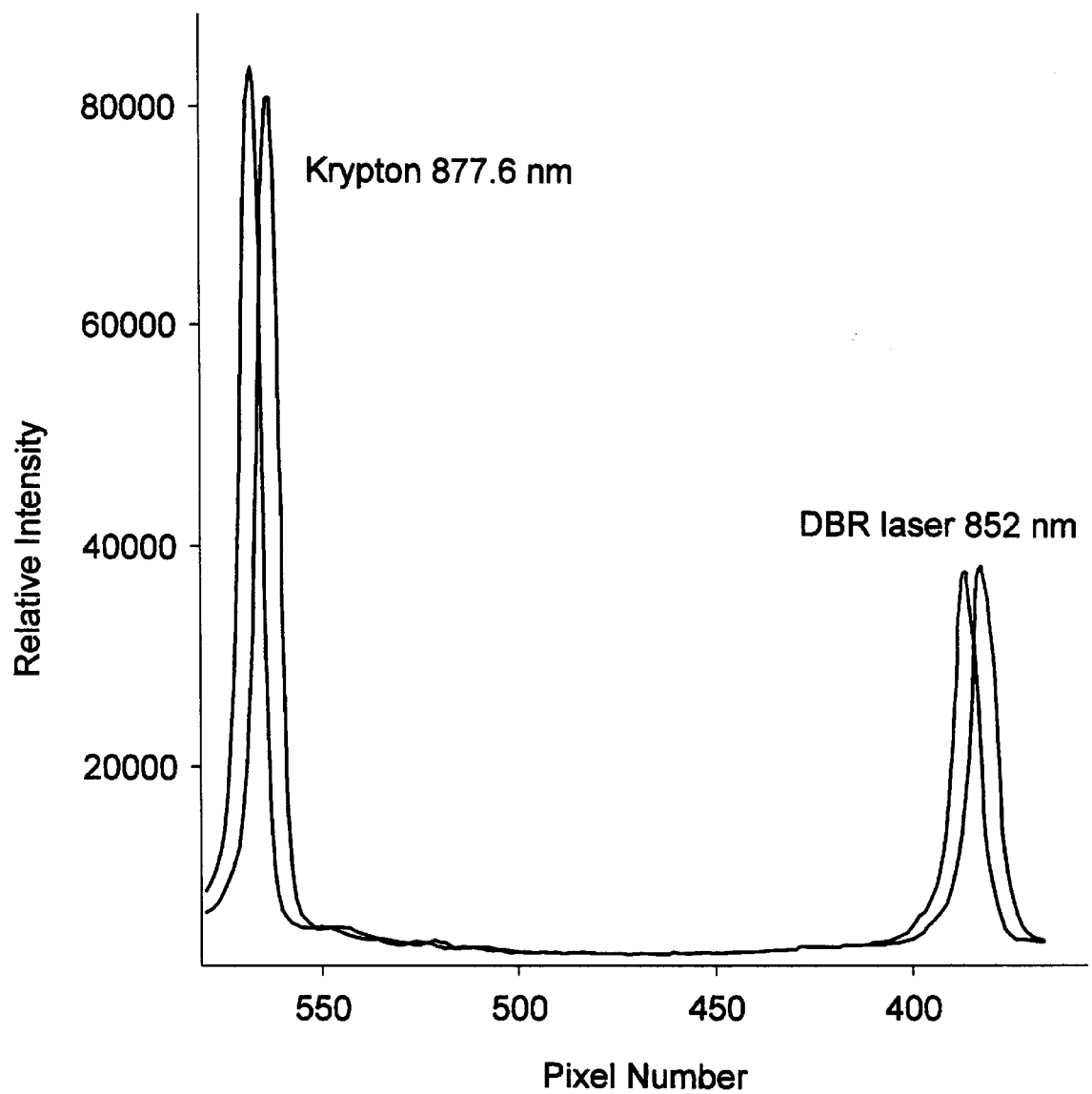
FIG. 4 is a plot of NIR spectra of DBR laser line and Krypton reference emission line acquired at 24 C (right) and 35 C (left). Spectra are acquired using Raman experimental setup. No CCD pixel binning is performed.

The above experiment is repeated after substituting a DBR diode laser for the index guided diode laser (FIG. 1a). No evidence for mode hopping is observed during the acquisition of the 120 toluene spectra. To further test the DBR laser stability, the spectrum of toluene is acquired (at 3 cm$^{-1}$ resolution) sequentially every ten minutes over the course of three days. During this experiment, the room temperature is also monitored. The 360 acquired spectra are shown in FIG. 2. No spectra have been omitted, and all spectra are uncorrected. Although the spectra appear identical at first glance, closer examination reveals some slight drift in the Raman peak positions relative to the CCD pixel number. FIG. 3 displays the apparent frequency shift of the strongest toluene mode at 1004 cm$^{-1}$ as a function of time and room temperature. During the first 1000 minutes, the room temperature decreases rapidly from 25.0° C. to 24.0° C. Simultaneously, the Raman peak shifts to higher frequency by 1.9 cm$^{-1}$. Over the remaining 2600 minutes, the room temperature begins to stabilize, only decreasing another 0.7 degrees. During this time the laser frequency does not vary by more than 0.25 cm$^{-1}$. The temperature controller is set to control the diode laser at –10° C. throughout the experiment. A thermocouple mounted in the diode laser package is used to maintain this control loop and its readout did not vary from –10° C. (0.1 degree accuracy) over the course of the experiment. In order to determine whether the frequency drift is due to the laser or the spectrograph, the spectrum of the laser line is acquired by diffusely reflecting the laser output into the collection fibers while also illuminating the collection fibers with the 877.6 nm emission line from a Krypton reference light. After acquiring the spectrum, the spectrograph baseplate is heated to 35° C. using a heat gun, and then a second spectrum is collected. The two overlaid spectra are shown in FIG. 4. The effect of heating the spectrograph is to shift both lines by 4 pixels on the CCD detector. This would correspond to an apparent frequency decrease with an increase in temperature. Applicants believe that this shift is due to a change in the focal point of the spectrograph's off-axis toroidal mirrors due to the thermal expansion of the metal baseplate. Hence the apparent frequency drift in the long term Raman experiment (FIG. 2) is not due to the laser, but rather the spectrograph. The absence of any mode hops during the course of the long term Raman experiment further confirms the temporal stability of the DBR laser output.

Indeed, Applicants used the DBR laser for the past twelve months and still have not observed a mode hop during the acquisition of a Raman spectrum. Applicants found, however, that with a DBR laser it is possible to induce a mode hop during a Raman acquisition by deliberately varying the drive current by large amounts (20–30%). During a spectral acquisition, the drive current to a diode laser can be set at a certain level (current mode) or set via a feedback loop which maintains a certain optical power output (light mode). When in light mode, the drive current may vary by as much as 1% in order to maintain optical output power at a certain level. This is true for both index guided and DBR lasers. In the case of index guided diode lasers, running the laser in light mode increases the number of mode hops relative to running the laser in constant current mode. With the DBR laser, the small current excursions which may occur when the laser is in light mode during a Raman acquisition are not significant enough to result in a mode hop.

Figure 5A:
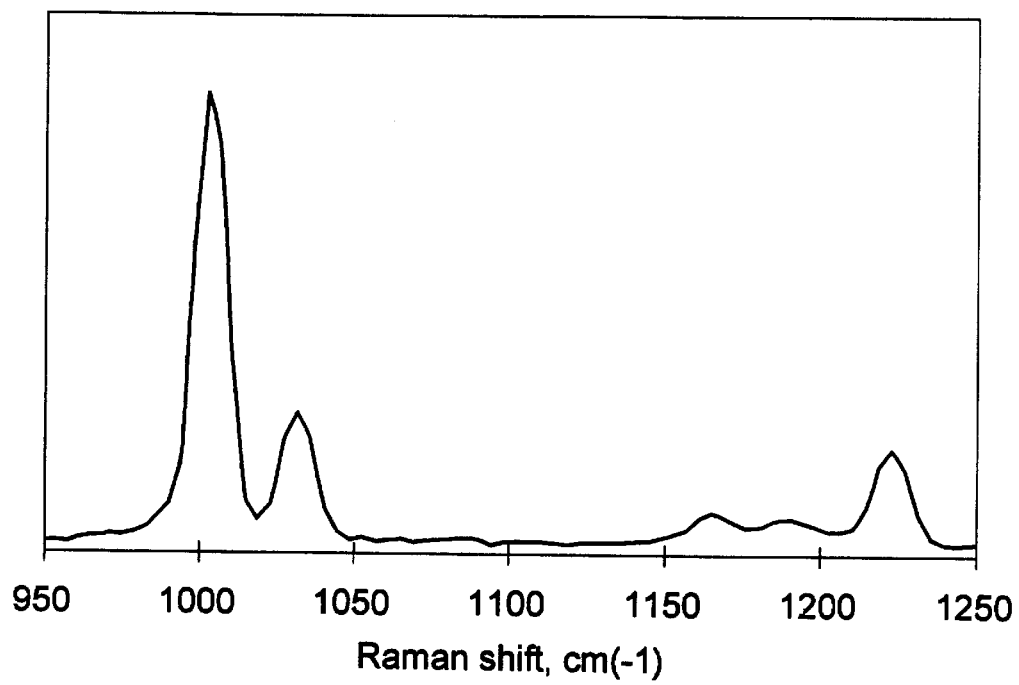
FIGS. 5a and 5b are plots of Raman spectra of toluene acquired using a DBR laser (FIG. 5a) and an index guided diode laser (FIG. 5b). For each spectrum, the laser temperature is initially set at −10° C. and is increased rapidly from −10° C. by 20°–30° C., held for several seconds, before returning to −10° C. and acquiring the spectrum. Only the index guided laser exhibits frequency hysteresis as a result of the temperature jump. Six representative spectra are shown in each plot.
Figure 5B:
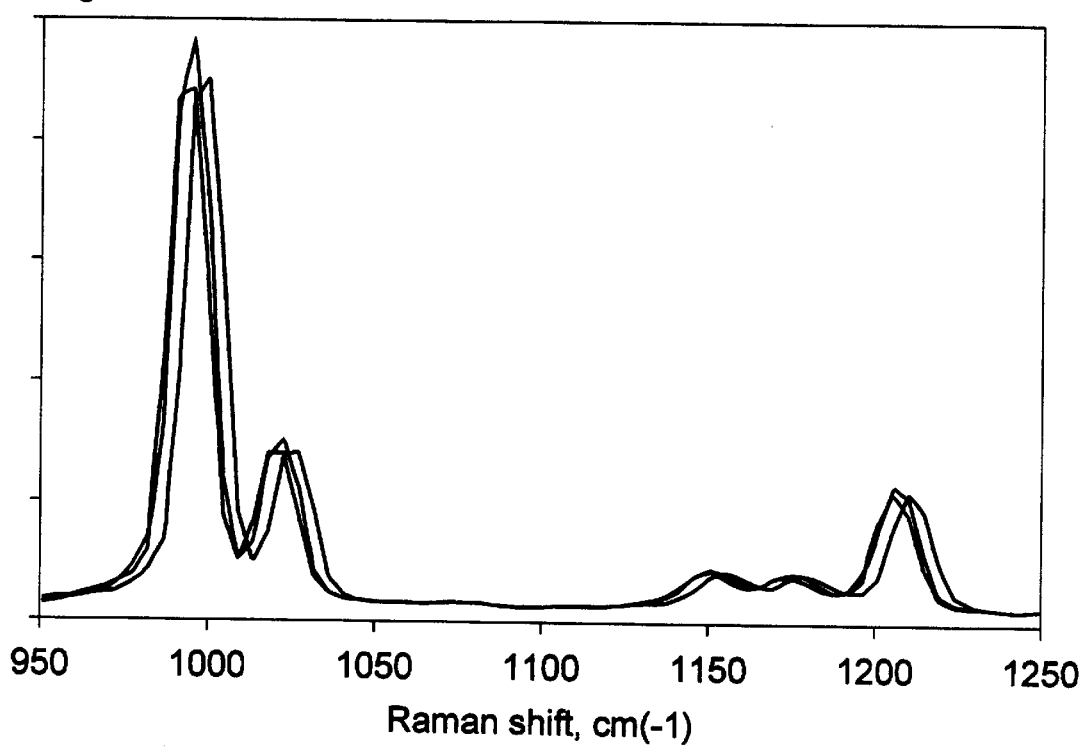

In order to compare the frequency hysteresis of the index guided and DBR diode lasers as a function of laser temperature, the Raman spectrum of toluene is acquired at the same temperature both before and after a large temperature jump (i.e., the temperature controller is adjusted to increase the temperature by 20°–30° C. and then returned to the original temperature). This process is repeated twenty times. The results are shown in FIGS. 5a and 5b. In the case of the DBR laser (FIG. 5a) no changes in the spectra are observed, indicating the absence of any hysteresis. The index guided diode laser (FIG. 5b) yields several spectra which are shifted by a few wave numbers. The shifts are much smaller than observed during the above mentioned mode hops, but are still large enough to introduce a significant statistical uncertainty into a process control application. This experiment is repeated, but instead of just inducing a temperature jump via the thermoelectric cooler, the temperature is changed by shutting down the laser and allowing it to come to room temperature before restarting it and cooling it back to –10° C. This process mimics what would be an ordinary shut down in either an industrial or research lab setting. In such a case, the operator would prefer that restart of the system would result in a return to the initial conditions. In the case of the DBR laser over the course of all 20 trials, this is the case. For the index guided diode laser, small frequency shifts occur 4 out of 20 times.

All laser diodes emit a broadband incoherent emission both below and above the lasing threshold. As the laser power is increased the broadband emission output remains constant. For an index guided laser, the broadband emission corresponds to a ~0.1 mW output with a bandwidth (FWHM) of 25 nm. It is a common practice to initially filter the laser using a narrow bandpass dielectric filter. For the index guided diode laser, even after filtering, the remnants of the emission can be seen in the Raman spectrum as "wings" off to the side of the main laser line (FIG. 3). Regardless of how the dielectric filter is angle tuned, applicants have found that it is not possible to completely eliminate these emission wings using the described dielectric filters.

Figure 6A:
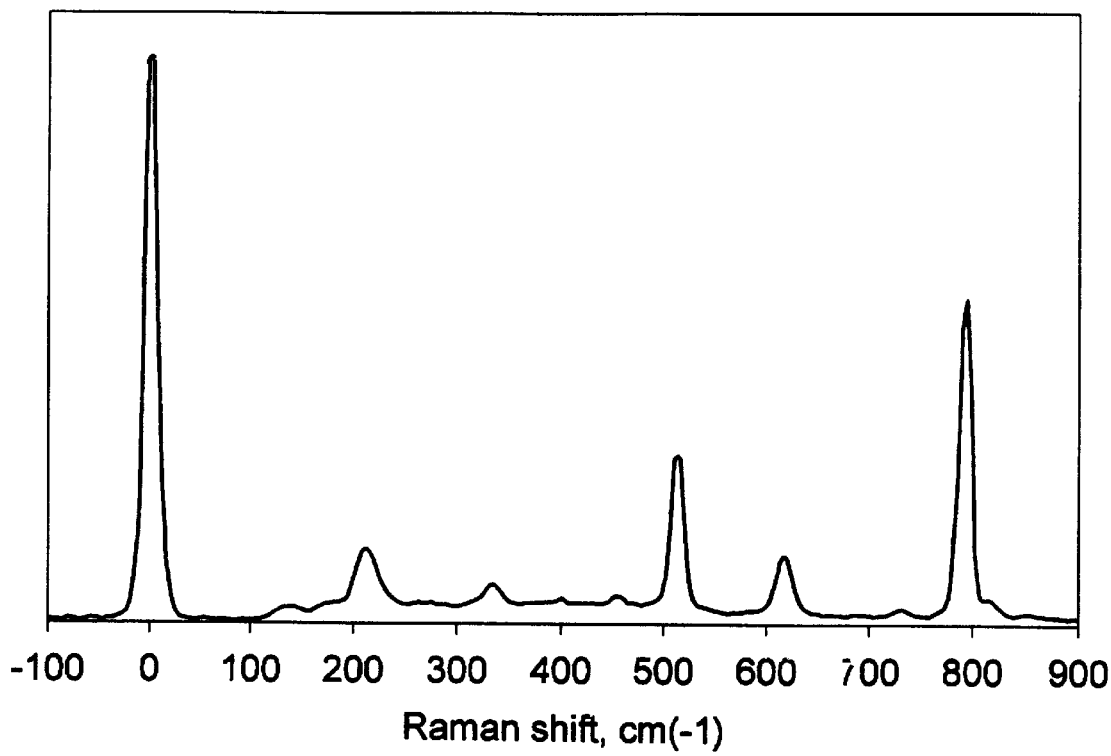
FIG. 6a is a plot of Raman spectrum of toluene including the filtered DBR laser line (Raman shift of 0). For the DBR laser, the broadband emission is completely filtered out.
Figure 6B:
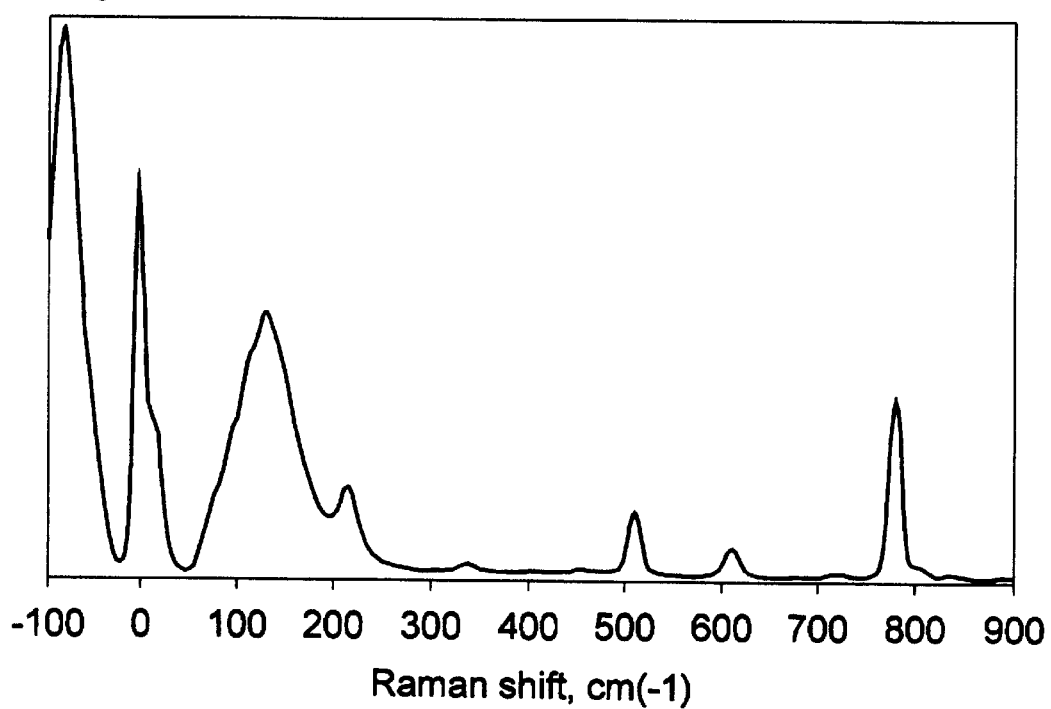
FIG. 6b is a plot of Raman spectrum of toluene including the filtered index guided diode laser line (Raman shift of 0). The broadband emission obscures the low frequency mode.

If the filters are properly tuned, the intensity of the wings can be lowered to approximately the intensity of the Raman scattering. Hence FIG. 6 represents a best case scenario for the index guided diode laser. At this intensity, the emission is unlikely to affect the signal-to-noise ratio significantly. However, slight changes in the dielectric filter angle or even mode hops can result in a significant increase in intensity of the emission wings. Even with the best case scenario shown in FIG. 6, it is still obvious that low frequency modes would be obscured by the emission level.

As shown at the top of FIG. 6, the results for the DBR laser differ markedly. Although the DBR laser also has an emission background, its intensity is initially much smaller than that of the index guided diode laser. Filtering with a dielectric filter completely eliminates the emission background from the Raman spectrum. This allows even low frequency vibrations to be observed and quantified. Note that the elimination of the broadband emission is dependent on the amount of radiation which is reflected/scattered into the collection fibers which is dependent upon the sampling geometry, the sample and the sample container, as well as the intensity of the radiation. For these two experiments, only the lasers are interchanged while the sampling remained constant.

MODIFICATIONS

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

Reference to documents made in the specification is intended to result in such patents or literature being expressly incorporated herein by reference.

What is claimed is:

1. Apparatus for the analysis of fluids comprising
   a) an excitation source comprising a Distributed Bragg Reflector diode laser;
   b) fluid sample holding means located to receive radiation from said laser through a fluid sample in said sample holding means;
   c) detection means comprising a spectrograph and a charge coupled detector operatively positioned to receive Raman radiation from said fluid sample.

2. The apparatus of claim 1 wherein said laser operating through said sample emits radiation at 852 nm.

3. The apparatus of claim 1 wherein the laser has an internal grating.

4. The apparatus of claim 3 wherein the detection means is operatively coupled to the sample holding means by fiber optic.

5. The apparatus of claim 4 wherein a holographic notch filter is positioned between the sample holding means and the spectrograph so as to filter Raman radiation from said sample.

6. A process for the analysis of fluids comprising:
   a) providing an excitation source comprising a Distributed Bragg Reflector diode laser;
   b) providing a fluid sample, in sample holding means, located to receive radiation from said laser through the sample;
   c) providing detection means comprising a spectrograph and a charge coupled detector operatively positioned to receive Raman radiation from said sample;
   d) operating said laser to provide radiation which passes into said fluid sample to produce a Raman signal which is received, at least in part, by said detection means;
   e) outputting a signal from said detection means indicative of the composition of at least one component in said fluid.

7. The process of claim 6 wherein the laser has an internal grating.

8. The process of claim 7 wherein said laser emits radiation at 852 nm.

9. The process of claim 6 wherein said fluid comprises a hydrocarbon.

10. The process of claim 7, wherein said fluid comprises a hydrocarbon.

11. The process of claim 6 wherein said fluid comprises toluene.

12. The process of claim 6 wherein said fluid comprises a motor hydrocarbon fuel.

13. The process of claim 8 wherein said fluid comprises a motor hydrocarbon fuel.

14. The process of claim 6 wherein the fluid comprises a hydrocarbon stream feeding, or produced by, a refinery process.

15. The process of claim 14 wherein the hydrocarbon stream is selected from streams derived from blending, reforming, hydrotreating, extraction, distillation, and petrochemical production processes.

* * * * *